(12) United States Patent
Patel

(10) Patent No.: US 8,636,715 B2
(45) Date of Patent: Jan. 28, 2014

(54) HIGH TORQUE, LOW PROFILE CATHETERS AND METHODS FOR TRANSLUMINAL INTERVENTIONS

(75) Inventor: Kaushik Patel, Poway, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 2018 days.

(21) Appl. No.: 11/534,895

(22) Filed: Sep. 25, 2006

(65) Prior Publication Data

US 2008/0125748 A1 May 29, 2008

(51) Int. Cl.
*A61M 25/00* (2006.01)

(52) U.S. Cl.
USPC ........................................ 604/523; 604/529

(58) Field of Classification Search
USPC ............................... 604/523, 529, 96.01, 158
See application file for complete search history.

(56) References Cited

U.S. PATENT DOCUMENTS

| | | | |
|---|---|---|---|
| 4,774,949 A | 10/1988 | Fogarty | |
| 5,830,222 A | 11/1998 | Makower | |
| 6,068,638 A | 5/2000 | Makower | |
| 6,159,225 A | 12/2000 | Makower | |
| 6,190,353 B1 | 2/2001 | Makower et al. | |
| 6,231,587 B1 | 5/2001 | Makower | |
| 6,283,951 B1 | 9/2001 | Flaherty et al. | |
| 6,355,027 B1 * | 3/2002 | Le et al. ........................ | 604/525 |
| 6,375,615 B1 | 4/2002 | Flaherty et al. | |
| 6,508,824 B1 | 1/2003 | Flaherty et al. | |
| 6,544,230 B1 | 4/2003 | Flaherty et al. | |
| 6,579,311 B1 | 6/2003 | Makower | |
| 6,602,241 B2 | 8/2003 | Makower et al. | |
| 6,655,386 B1 | 12/2003 | Makower et al. | |
| 6,660,024 B1 * | 12/2003 | Flaherty et al. ............... | 600/439 |
| 6,685,648 B2 | 2/2004 | Flaherty et al. | |
| 6,709,444 B1 * | 3/2004 | Makower ....................... | 606/198 |
| 6,726,677 B1 | 4/2004 | Flaherty et al. | |
| 6,746,464 B1 | 6/2004 | Makower | |

OTHER PUBLICATIONS

Bolia et al., "Percutaneous Transluminal Angioplasty of Occlusions of the Femoral and Popliteal Arteries by Subintimal Dissection" Cardiovasc. Intervent Radiol. 13:357-63 (1990).
Reekers, J.A., Percutaneous Intentional Extraluminal Recanalisation of the Femoropopliteal Artery, Eur. J. Vasc. Surg., 8:723-28 (1994).
Kimura, B.J., et al. "Subintimal Wire Position During Angioplasty of a Chronic Total Coronary Occlusion: Detection and Subsequent Procedural Guidance by Intravascular Ultrasound," Cathet. Cardiovasc. Diagn., 35(3), 262-65 (1995).

* cited by examiner

*Primary Examiner* — Kevin C. Sirmons
*Assistant Examiner* — Phillip Gray

(57) ABSTRACT

Catheter devices having low profile shafts and laterally deployable members (e.g., cannulas, needles, etc.) that may be extended or advanced laterally from the catheter shaft. Also disclosed are methods for bypassing a vascular obstruction (e.g., a chronic total occlusion or other full or partial obstruction) wherein a guidewire is entrapped in a subintimal space adjacent to the obstruction. A catheter of the foregoing character is advanced over the entrapped guidewire and into the subintimal space. The laterally deployable member is then advanced or extended from the subintimal space back into the true lumen of the blood vessel distal to the obstruction. A second guidewire is then advanced through or along the laterally deployable member. The catheter and first guidewire are then removed and one or more working device(s) (balloons, atherectomy devices, setnts, etc.) is/are advanced over the second guidewire and used to establish a subintimal bypass channel through which blood may flow around the obstruction.

10 Claims, 8 Drawing Sheets

HIGH TORQUE, LOW PROFILE CATHETERS AND METHODS FOR TRANSLUMINAL INTERVENTIONS

FIELD OF THE INVENTION

The present invention relates generally to methods and apparatus for medical treatment and more particularly to catheters and related methods for vascular and other transluminal interventional procedures.

BACKGROUND

Catheters Having Laterally Deployable Members

The prior art has included a variety of intravascular catheters that have laterally deployable members (e.g., wires, needles, other catheters, probes, etc.) which advance or extend laterally from the body of the catheter. In some applications, these catheters are used to direct a laterally deployable member into a furcation, side branch or other angulation vessel. In other applications, the laterally deployable members are caused to penetrate through tissue or other matter within the body to reach some desired target location.

U.S. Pat. No. 4,774,949 (Fogarty) describes a deflector guiding catheter having a lumen that extends through the catheter and terminates distally in a side outlet opening. As the lumen approaches the side outlet opening, it smoothly curves from axial to angular orientation so as to deflect a member (e.g., a guidewire or another catheter) out of the side outlet opening such that the member may then advance laterally from the catheter body. In applications where it is desired to deflect the member into a side branch or other angulation vessel, the side outlet port is positioned in registry with the mouth of the side branch or angulation vessel. The shape and curvature of the distal portion of the lumen is designed to support the laterally deployable member during advancement and to prevent backup movement of the laterally deployable member during placement, dilatation and/or extrusion.

U.S. Pat. Nos. 5,830,222 (Makower), U.S. Pat. No. 6,068,638 (Makower), U.S. Pat. No. 6,159,225 (Makower), U.S. Pat. No. 6,190,353 (Makower, et al.), U.S. Pat. No. 6,283,951 (Flaherty, et al.), U.S. Pat. No. 6,375,615 (Flaherty, et al.), U.S. Pat. No. 6,508,824 (Flaherty, et al.), U.S. Pat. No. 6,544,230 (Flaherty, et al.), U.S. Pat. No. 6,655,386 (Makower et al.), U.S. Pat. No. 6,579,311 (Makower), U.S. Pat. No. 6,602,241 (Makower, et al.), U.S. Pat. No. 6,655,386 (Makower, et al.), U.S. Pat. No. 6,660,024 (Flaherty, et al.), U.S. Pat. No. 6,685,648 (Flaherty, et al.), U.S. Pat. No. 6,709,444 (Makower), U.S. Pat. No. 6,726,677 (Flaherty, et al.) and U.S. Pat. No. 6,746,464 (Makower) describe a variety of catheter devices having laterally deployable tissue penetrating members (e.g., wires, needles, energy emitting penetrators, cannulae, etc.). These catheter devices are positionable within natural or man made body passages (e.g., blood vessel lumens, other lumens, passages, spaces, cul-de-sacs, tracts, subintimal spaces, etc.) and the laterally deployable tissue penetrating members are advanced to target locations outside of the passage in which the catheter is positioned. These types of catheter devices are useable in many types of interventions, including the delivery of substances (e.g., drugs, biologics, cells, genes, contrast media or other diagnostic or therapeutic substances), articles or devices to target locations within the body, passage of guidewires and/or catheters for accessing target locations, bypassing of obstructions, re-entry into a true lumen of a blood vessel from a subintimal space, etc.

Treatment of Chronic Total Occlusions

One particular example of a procedure in which catheter devices of the above-described type have been used is in the bypassing of chronic total occlusions, or CTOs. A CTO is a complete or nearly complete blockage in an artery. In many CTO cases, a guidewie can be advanced around the obstructive lesion, but this typically results in the distal portion of the guidewire penetrating or dissecting into the artery wall such that a distal portion of the guidewire becomes entrapped in a subintimal space (e.g., a dead-end channel created by advancement of the guidwire within the artery wall next to the obstruction). When such subintimal entrapment of the guidewire occurs, it is necessary to cause the distal end of that guidewire, or alternatively a separate guidewire, to reenter the true lumen of the artery downstream of the obstruction.

Techniques for guiding re-entry of subintimally entrapped guidewires into the true lumen of an artery have been known for quite some time. Prior to 1990, subintimal passage of a CTO was typically performed only if the guidewire had accidentally entered the subintimal space.

In 1990, Bolia, et al. reported a catheter-based technique for intentional extraluminal recanalization of a femoralpopliteal CTO. Specifically, Bolia, et al. reported that in cases where the guidewire failed to naturally re-enter the true lumen distal to the obstruction, a curved catheter could be inserted into the subintimal space and used to guide the distal end of the guidewire back into the true lumen. Bolia et al., *Percutaneous Transluminal Angioplasty of Occlusions of the Femoral and Popliteal Arteries by Subintimal Dissection*, Cardiovasc. Intervent. Radiol. 13:357-63 (1990).

In 1994, Reekers, et al. reported work conducted between 1990 and 1992 wherein a custom made 5 French catheter having a tip angle of 30, 50 or 70 degrees was inserted into the subintimal space and used to guide reentry of the guidewire into the true lumen of the artery distal to the CTO. Reekers, J.A., Percutaneous Intentional Extraluminal Recanalisation of the Femoropopliteal Artery, Eur. J. Vasc. Surg., 8:723-28 (1994).

In 1995, Kimura et all. reported that the use of intravascular ultrasound (IVUA) could be helpful in navigating subintimally entrapped guidewires back into the true lumen of the artery. Kimura, B.J., et al., *Subintimal Wire Position During Angioplasty Of A Chronic Total Coronary Occlusion: Detection And Subsequent Procedural Guidance By Intravascular Ultrasound*, Cathet. Cardiovasc. Diagn., 35(3), 262-65 (July 1995).

Also in 1995, a initial United States patent application was filed describing and claiming catheters that had laterally deployable members (e.g., needles or cannulae) for penetrating from a body passage in which the catheter is positioned (e.g., a blood vessel lumen, body cavity or other passage or space such as a subintimal tract created by a guidewire passing a CTO) to some target location outside of that body passage. In some embodiments, these catheters included orientation elements such as on-board imaging devices (e.g., intravascular ultrasound imaging) and/or imageable markers that could be used by the operator to determine the rotational orientation of the catheter in situ such that the operator could adjust the rotational orientation of the catheter as needed before deployment of the laterally deployable member, thereby facilitating subsequent extension or advancement of the laterally deployable member into a desired target location (e.g., back into the true lumen of the blood vessel) rather than to some other undesired location. A number of United States and non-United States patents have issued from or claim priority to this originally filed 1995 patent application, including but not limited to U.S. Pat. No. 5,830,222 (Makower), U.S. Pat. No. 6,068,638 (Makower), U.S. Pat. No.

6,746,464 (Makower), U.S. Pat. No. 6,231,587 (Makower), U.S. Pat. No. 6,190,353 (Makower et al.), U.S. Pat. No. 6,655,386 (Makower et al.), the entire disclosures of which are expressly incorporated herein by reference.

Catheters useable for guiding reentry of subintimally entrapped guidewires are being developed and/or sold commercially. For example, the Outback™ catheter (Lumend Inc. of Redwood City, Calif.) is a relatively simple catheter that has a laterally deployable needle. The catheter is inserted into the subintimal space with the needle in its retracted position. Thereafter, the laterally deployable needle is advanced from the subintimal space into the true lumen. A guidewire is then advanced through the lumen of the needle into the true lumen. The Outback™ catheter also includes an imageable marker that is configured to indicate the direction in which the needle will advance so that the operator may adjust the rotational orientation of the catheter in situ to facilitate subsequent advancement of the needle into the true lumen rather than to some other undesired location, substantially as described in various U.S. patents including U.S. Pat. No. 6,655,386 (Makower et al.).

The Pioneer™ catheter (Medtronic Vascular, Inc. of Santa Rosa, Calif.) is also a catheter that has a laterally deployable needle that may be used to penetrate from the subintimal space into the true lumen such that a guidewire may then be advanced through the needle and into the true lumen of the artery. Additionally, the Pioneer™ catheter incorporates an on-board IVUS device which provides an image that may be used by the operator to adjust the placement and rotational orientation of the catheter in situ to facilitate subsequent advancement of the needle into the true lumen rather than to some other undesired location, substantially as described in various U.S. patents including U.S. Pat. No. 6,655,386 (Makower et al.). The needle of the Pioneer™ catheter is elastic and biased to a curved configuration. A substantially rigid needle housing is mounted within the catheter body and the distal portion of the needle resides within such needle housing while in its retracted position. The curvature of the needle mates with the curvature of the needle housing, thereby causing the needle to be rotationally constrained in its intended rotational orientation. Also, the needle housing is radiographically imageable and curved in the direction of the side outlet opening through which the needle exits the catheter body. Thus, a radiographic image of the needle housing itself may be used (alone or in combination with the catheter's IVUS imaging capability) to guide and verify the positioning and rotational orientation of the catheter in situ to facilitate subsequent advancement of the needle into the true lumen rather than to some other undesired location. Moreover, the needle housing is sufficiently rigid and configured to provide support for the needle when the needle is in its advanced position.

There remains a need in the art for the development of new catheter devices and methods that may be used for re-entering the true lumen of an artery from a subintimal space and/or for other applications where a catheter is positioned in a natural or man-made body passage and it is desired to extend or advance a laterally deployable member from the catheter to some target location outside of the body passage within which the catheter is positioned.

SUMMARY OF THE INVENTION

In accordance with the present invention there is provided a catheter device comprising i) an elongate catheter body, at least a portion of which comprises a) a core member having at least one lumen extending therethrough, b) a substantially cylindrical braided layer disposed about the core member and c) an outer layer disposed about said braided layer and ii) a laterally deployable member that is advanceable or extendable laterally from the catheter body. At least the core member of the catheter body is formed of material that is sufficiently lubricious to allow a guidewire or other member to advance through the lumen of the core member without the need for placement of a lubricious liner within the lumen. Also, in at least some embodiments, the construction of the catheter body is such that it has a diameter of no more than 0.080 inch and in some cases in the range of from about 0.067 inch to abut 0.080 inch. In some embodiments, the diameter of the catheter body is small enough to allow it to pass through a standard 6 French introducer sheath. In some embodiments, the laterally deployable member may comprises a tubular member (e.g., a cannula or hollow needle) and may be formed of elastic or superelastic material and biased to a curved configuration. Also, in some embodiments, one or more imageable marker(s) or other imageable elements of the catheter device may be imaged by radiographic or other imaging means and may be configured to indicate the direction or trajectory on which the laterally deployable member will extend or advance from the catheter body. An image of such marker or other element may thus be used by the operator to adjust the position and/or rotational orientation of the catheter body in situ to increase the likelihood that the laterally deployable member will subsequently extend or advance into a desired target location (e.g., within the true lumen of a blood vessel) rather than to some other unintended location.

Further in accordance with the invention, there is provided a method for bypassing an obstruction in a blood vessel (e.g., a chronic total occlusion or other full or partial obstruction). In this method, a first guidewire is advanced into the blood vessel such that a distal portion of the first guidewire becomes positioned within a subintimal space adjacent to the obstruction. Thereafter, a catheter device having a laterally deployable member is advanced over the first guidewire such that a distal portion of the catheter is within the subintimal space. This catheter device may be constructed in the manner described in the immediately preceding paragraph hereabove. With the catheter positioned in the subintimal space, the laterally deployable member is then advanced or extended from the subintimal space into the true lumen of the blood vessel distal to the obstruction. Thereafter, a second guidewire is advanced through or along the laterally deployable member and into the true lumen of the blood vessel distal to the obstruction. The laterally deployable member is then retracted and the catheter device and the first guidewire are removed, leaving the second guidewire in place such that it extends through the true lumen of the blood vessel proximal to the obstruction, through the subintimal space and back into the true lumen of the blood vessel distal to the obstruction. Thereafter, at least one working device (e.g., dilation balloon, atherectomy device, stent delivery device) is advanced over the second guidewire and used to modify (e.g., dilate, enlarge, debulk, stent, etc.) the subintimal space. This creates a bypass conduit through which blood may flow from the true lumen of the blood vessel proximal to the obstruction, through the subintimal space and back into the true lumen of the blood vessel distal to the obstruction.

Further aspects, details and embodiments of the present invention will be understood by those of skill in the art upon reading the following detailed description of the invention and the accompanying drawings.

BRIEF DESCRIPTION OF THE DRAWINGS

FIG. 2A is a cross-sectional view through line 2A-2A of FIG. 2.

FIGS. 4A-4G show steps in a method for using the catheter device of FIG. 1 to perform a transluminal, catheter-based bypass of a CTO in an artery.

DETAILED DESCRIPTION

The following detailed description, the accompanying drawings are intended to describe some, but not necessarily all, examples or embodiments of the invention. The contents of this detailed description and accompanying drawings do not limit the scope of the invention in any way.

Figure 1:
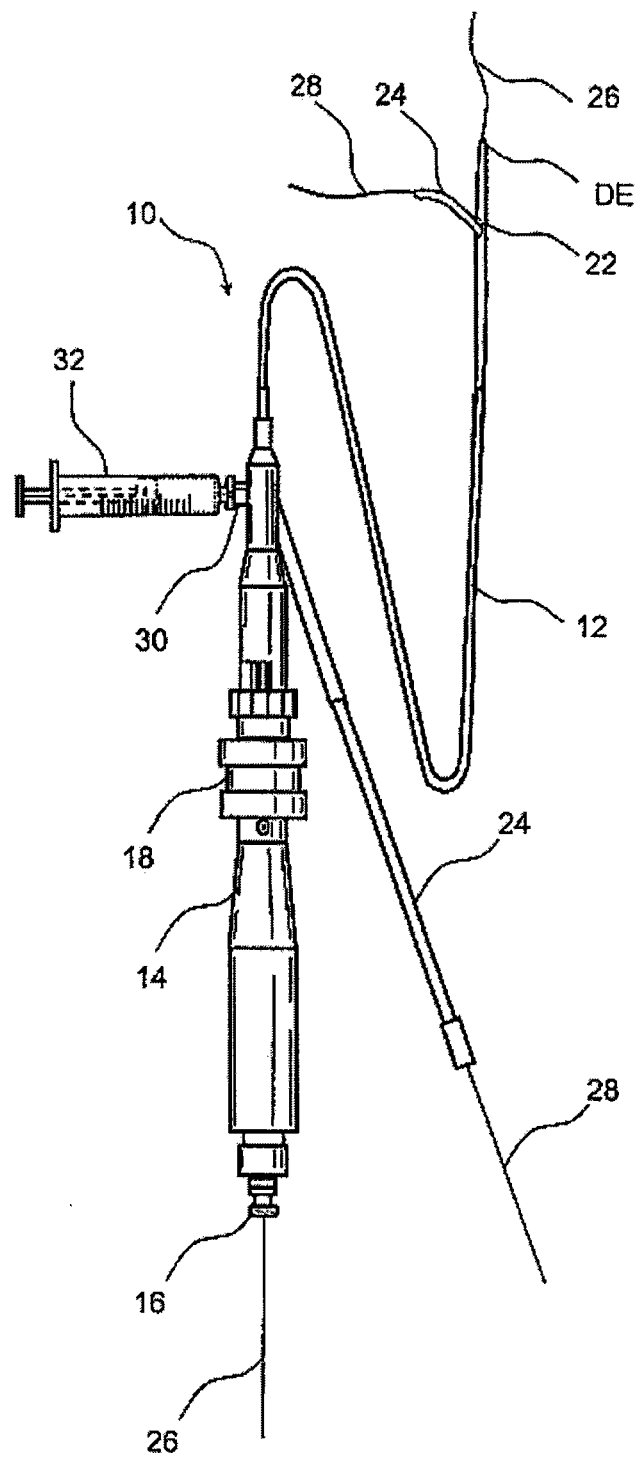
FIG. 1 is a side view of one embodiment of a high torque, low profile catheter device of the present invention.
Figure 2:
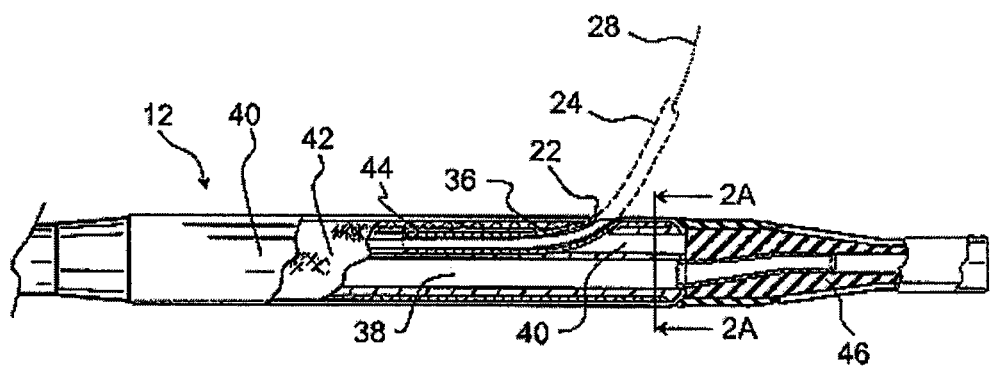
FIG. 2 is a partial cut away view of the distal end of the catheter device of FIG. 1.
Figure 2:
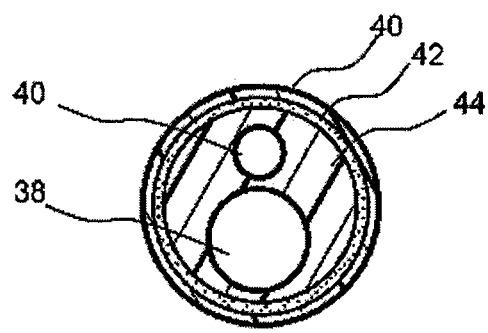
Figure 2B:
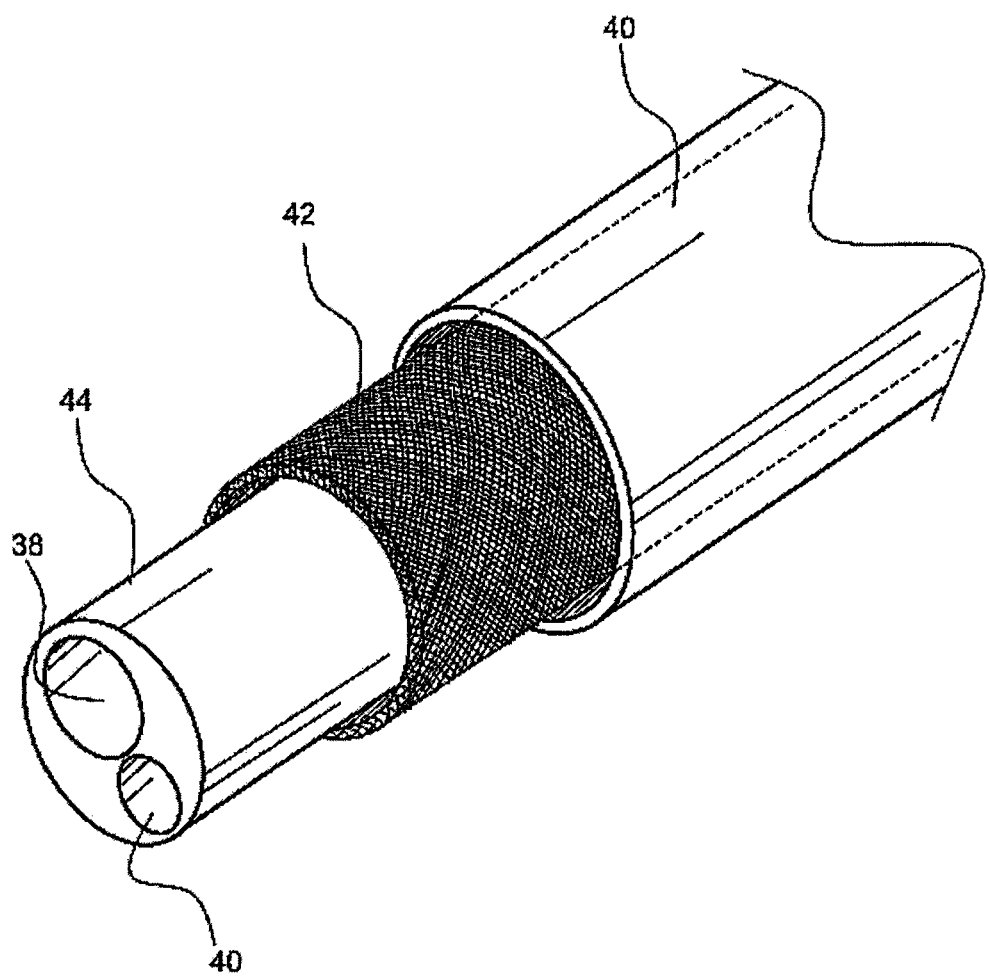
FIG. 2B is a partial cut away view showing components of the braided shaft of the catheter device of FIG. 1.

FIGS. 1-2B show one example of a catheter device 10 of the present invention. This catheter device 10 comprises an elongate catheter body 12 (e.g., a catheter shaft) having an atraumatic distal tip member 46 on its distal end DE and a handpiece 14 on its proximal end. As shown specifically in FIG. 2B, the catheter body 12 comprises a core member 44, a braid layer 42 surrounding the core member 44 and an outer layer 40 surrounding the braid layer 42. These components 40, 42, 44 of the catheter body 12 may be formed of materials that provide the desired strength and torque transmission while minimizing the overall diameter of the catheter body 12. For example, the core member 44 may comprise machined or extruded polyethylene (HDPE), ultra-high molecular weight polyethylene (UHMWPE) or polypropylene (PP). The braid layer 42 may be formed of stainless steel flat ribbon, ultra-thin wire or polymer fibers such as aramid fiber (Kevlar® available from E. I. Dupont de Nemours, Inc., Wilmington, Del.). The outer layer 40 may be formed of polymeric materials, metal or woven material including the same or different material as the first braid layer. In embodiments where the core member 44 is formed of HDPE, UHMWPE or PP, the inner surfaces of lumens 38, 40 are sufficiently smooth and lubricious as not to require disposition of a lubricious liner (such as a polytetrofluoroethylene/polyimid liner) therein. Because no liner is required, the overall diameter of the core member 44 may be smaller than would be possible if lumen liner(s) were required.

A first lumen 38 extends from a port 16 on the proximal end of the handpiece 14, through the handpiece 14, through the core member 44, through distal tip member 46, terminating in an opening in the distal end of the distal tip member 46. First lumen 38 may be used as a guidewire lumen for over-the-wire placement of the catheter 10 and/or it may be used for infusion/aspiration of substances via a syringe 32, infusion tube or other suitable infusion or aspiration device attached to port 30. A valve, cap or other closure apparatus (not shown) may be associated with port 16 to deter backflow of fluids out of port 16 when fluids are being infused through port 30. In rapid exchange embodiments of the catheter 10, it will be appreciated that, instead of lumen 38 extending proximally to port 16 on the proximal end of the handpiece 14, the lumen 38 may terminate proximally in a side port (not shown) formed in the side wall of catheter body 12.

A second lumen 40 extends from sidearm 28 on handpiece 14, through handpiece 14 and through the core member 14 at least to a side outlet opening 22 that is formed in the catheter body 12. As seen in FIG. 2, a curved tubular housing 36 is positioned within the second lumen 38 with the distal end of the needle housing 36 being positioned within or immediately adjacent to the side outlet opening 22. A laterally deployable member is moveable back and forth between a retracted position and an extended position. In the particular embodiment shown in the drawings, this laterally deployable member comprises a hollow cannula such as a needle 24 formed of elastic or supereleastic material (e.g., nickel-titanium alloy). A distal portion of this needle 24 is biased to a curved configuration. The needle 24 may have a maximum internal diameter of 0.017 inch (0.43 mm). A second guidewire 28, such as a 0.014 inch (0.36 mm) non-hydrophilically coated guidewire, may be advanced through sidearm 28, through the lumen of the needle 24 and out of the distal end of the needle 24. Alternatively, diagnostic or therapeutic substances, articles or devices may also be passed through the lumen of the needle 24. Examples of the types of substances, articles and devices that may be delivered through the lumen of the needle 24 include but are not limited to those described in U.S. Pat. Nos. 6,602,214 (Makower, et al.) or in copending U.S. patent application Ser. No. 10/411,891 (Lamson, et al.) and Ser. No. 11/279,771 (Lamson et al.), each such patent and patent application being expressly incorporated herein by reference.

When the needle 24 is in its retracted position, it is within the catheter body 12 with the curved distal portion of the needle 24 being situated within the curved housing 36. The curvature to which the needle 24 is biased may mate with the curvature of the housing 36, thereby deterring rotation of the distal portion of the needle 24 while it resides within the housing 36. In this manner, if the needle 24 has a side opening or bevel, such side opening or bevel may be maintained in a desired, known orientation. When the needle 24 is moved to its extended position, it will advance out of side outlet opening 22, as indicated in dotted lines on FIG. 2. A knob 18 on handpiece 14 controls movement of the needle 24 between its retracted position and its extended position. An adjustable or non-adjustable limiting member may also be provided to limit the distance to which the needle 24 extends out of side outlet opening 22. In some embodiments, the knob 18 may operate to advance the needle 18 in preset increments, for example up to seven 1 mm increments to a pre-determined mavimum extension of 7 mm.

In some embodiments, the curved housing 36 may be formed of metal or other imageable or radiopaque material and may additionally function as an imageable indicator marking the radial location of side outlet opening 22 and/or indicating the direction or trajectory on which the needle 24 will advance. In this manner, an image of the curved housing 36 may be used by the operator to adjust the position and rotational orientation of the catheter body 12 in situ to ensure, or at least improve the probability that, subsequent advancement of the needle 24 will cause the needle to advance in the direction of a desired trget location (e.g., into the true lumen of an adjacent artery) rather than to some other undesired location. Optionally, the catheter 10 may include other imageable markers and/or imaging apparatus and/or other orientation-indicating elements may be included to mark the radial location of side outlet opening 22 and/or to indicate the direction or trajectory on which the needle 24 will advance, examples of which are described in United States patent Nos. U.S. Pat. Nos. 5,830,222 (Makower), U.S. Pat. No. 6,068,638 (Makower), U.S. Pat. No. 6,159,225 (Makower), U.S. Pat.

No. 6,190,353 (Makower, et al.), U.S. Pat. No. 6,283,951 (Flaherty, et al.), U.S. Pat. No. 6,375,615 (Flaherty, et al.), U.S. Pat. No. 6,508,824 (Flaherty, et al.), U.S. Pat. No. 6,544,230 (Flaherty, et al.), U.S. Pat. No. 6,655,386 (Makower et al.), U.S. Pat. No. 6,579,311 (Makower), U.S. Pat. No. 6,602,241 (Makower, et al.), U.S. Pat. No. 6,655,386 (Makower, et al.), U.S. Pat. No. 6,660,024 (Flaherty, et al.), U.S. Pat. No. 6,685,648 (Flaherty, et al.), U.S. Pat. No. 6,709,444 (Makower), U.S. Pat. No. 6,726,677 (Flaherty, et al.) and U.S. Pat. No. 6,746,464 (Makower), which are incorporated herein by reference.

In comparison to the currently available Pioneer™ catheter (Medtronic Vascular, Inc., Santa Rosa, Calif.), the catheter body 12 is constructed in a manner that allows the outer diameter of the catheter body 12 to be reduced to approximately 0.067 inch, while maintaining the needed torque transmission capability for use in CTO procedures, such as the procedure shown in FIGS. 4A-4G, described in detail herebelow. Typically, catheters 10 of this invention will have outer diameters of from about 0.067 inch to abut 0.080. In this regard, the use of material such as HDPE, UHMWPE or PP, but still with the braided layer 42, allows the diameter of the catheter body 12 to be reduced as much as 1 French size while still providing all the other relevant properties that are desired for the performance of this catheter. Also, the catheter body 12 construction shown in FIG. 4 eliminates the need for expensive composite structure liners while still providing desirable flexibility. Additionally, the materials used in the construction of this catheter body 12 are highly processible making it feasible for the attachment of a distal tip member 46 that comprises a composite structure (e.g., a flexible thermoplastic (e.g., Pebax® polyether block amide disposed on a rigid platinum housing).

Because of its reduced outer diameter, the catheter 10 may be inserted through a standard 6 French introducer sheath (e.g., a 6 Fr. Avanti™ introducer sheath available from Johnson & Johnson/Cordis, Miami, Fla. or a 6 Fr. Super Sheath™ introducer available from Boston Scientific, Inc., Boston, Mass.) to a 7 to 8 Fr. Sheath as required of some prior art devices, thereby resulting in less patient trauma, greater flexibility and fewer post-procedure bleeding complications at the percutaneous puncture site.

Figure 3:
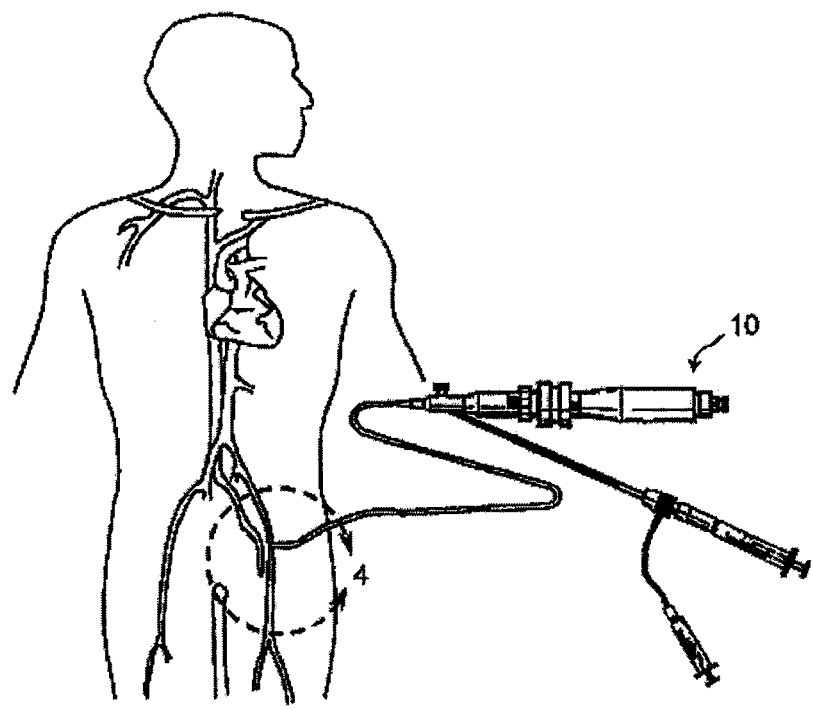
FIG. 3 is a schematic showing of a human subject having the catheter device of FIG. 1 operatively inserted into an artery of the lower extremity for the purpose of treating a CTO of that artery.
Figure 4:
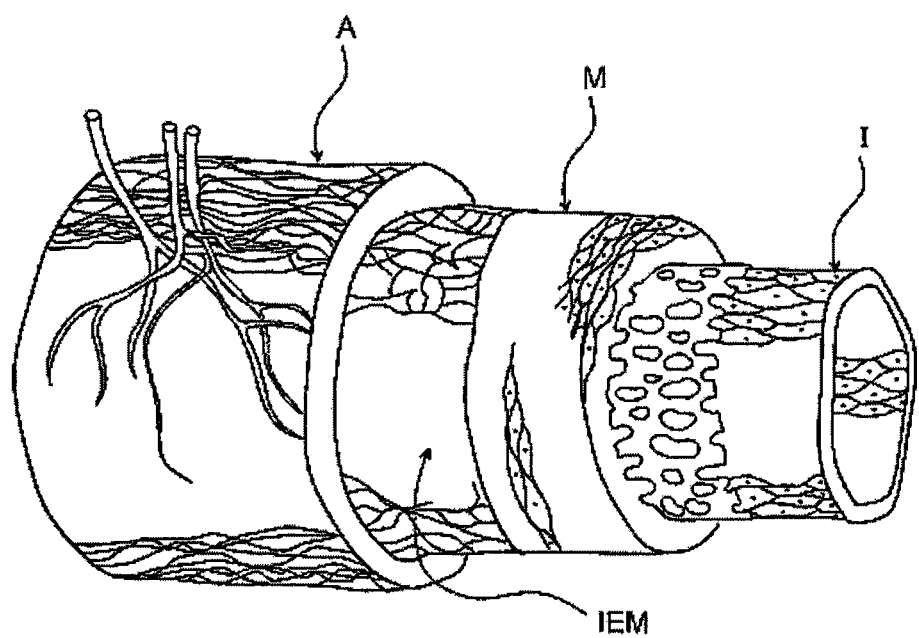
FIG. 4 is an anatomical diagram showing the histological layers of an artery.

FIGS. 3-4G show an example of a procedure in which the above-described catheter device 10 is used to treat a CTO of an artery of the lower extremity of a human subject. As specifically shown in FIG. 4, the wall of an artery typically consists of three layers, the tunica intima I ("intima"), tunica media M ("media") which is the thickest layer of the wall and the tunica adventitia A (adventitia). In some arteries an internal elastic membrane IEM is disposed between the media M and adventitia A.

Figure 4A:
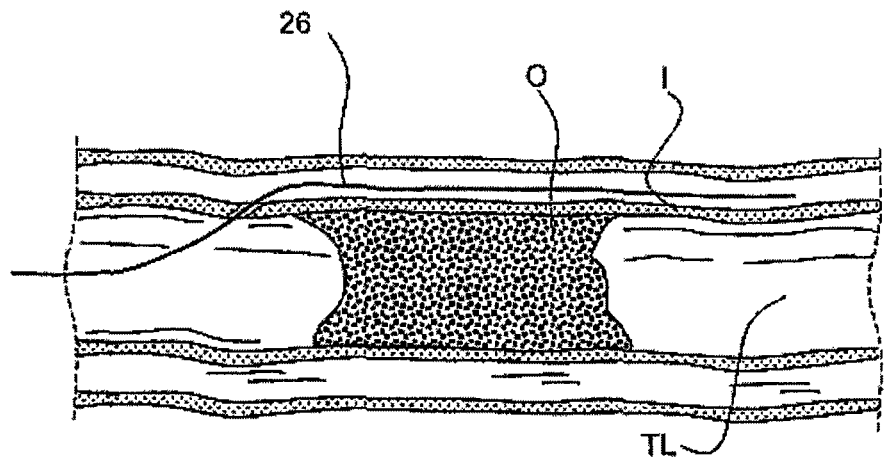

Initially, a percutaneous puncture is made into the femoral artery and a 6 French PTFE introducer is inserted in the direction of normal bloodflow through the artery. As seen in FIG. 4A, a guidewire 26 is advanced into a subintimal space adjacent to the obstruction O such that the distal end of the guidewire 26 is within the subintimal space, distal to the obstruction O.

Figure 4B:
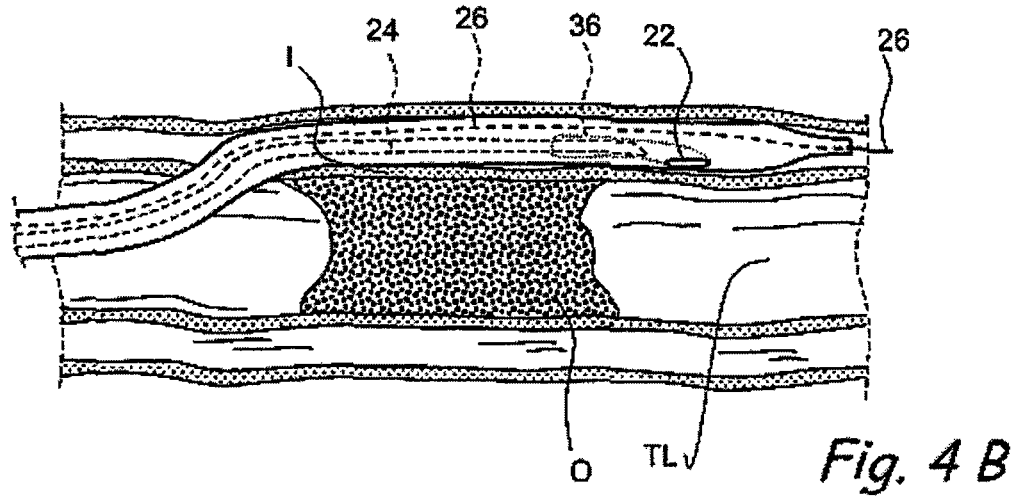

Thereafter, As seen in FIG. 4B, the catheter 10 of the present invention is advanced over the guidewire 26 while the needle 24 is in its retracted position within housing 36. The catheter 10 is advanced to a position where the side outlet opening 22 is distal to the obstruction O. Thereafter, fluoroscopy is used to image the curved radiopaque housing 36 (and/or other imageable marker(s) which indicate the radial position of the side outlet opening 22 and/or the direction or trajectory on which the needle will subsequently advance). This fluoroscopic image is then used to guide rotation of the catheter body 12 to cause the side outlet opening 22 and the needle 24 to be directed toward the true lumen TL of the artery.

Figure 4C:
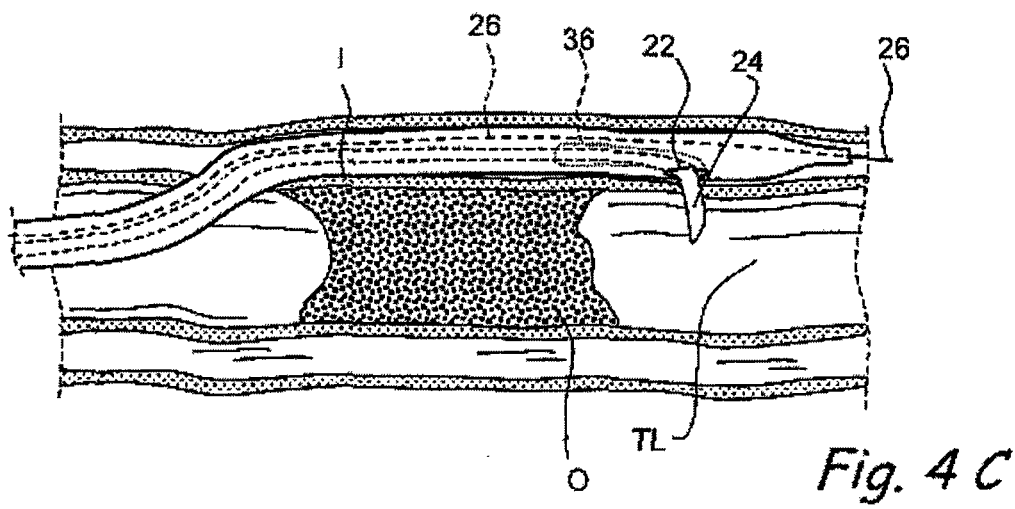
Figure 4:
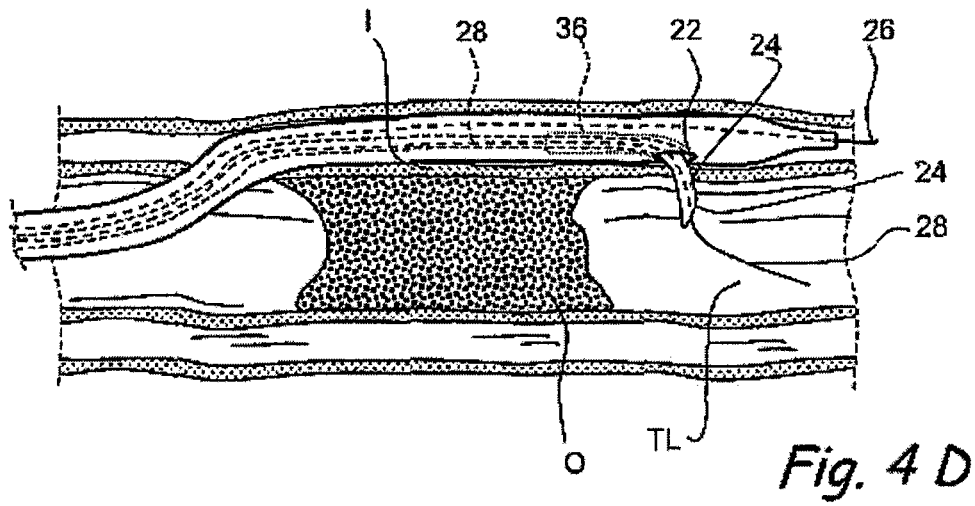
Figure 4:
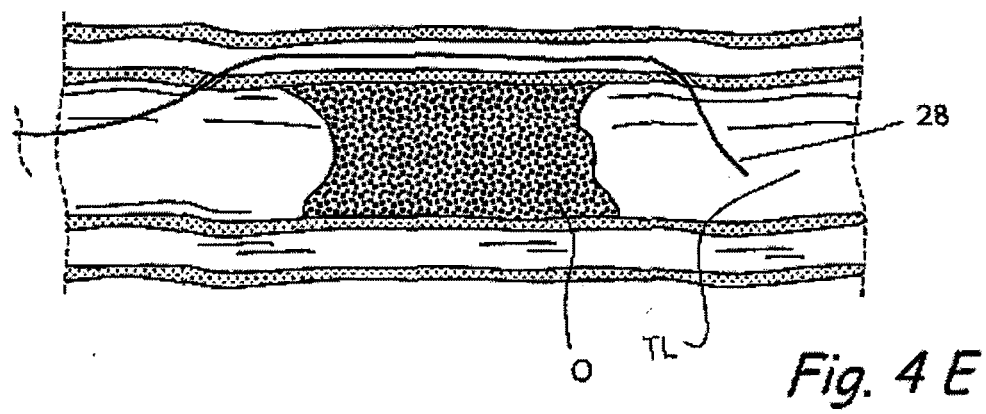
Figure 4:
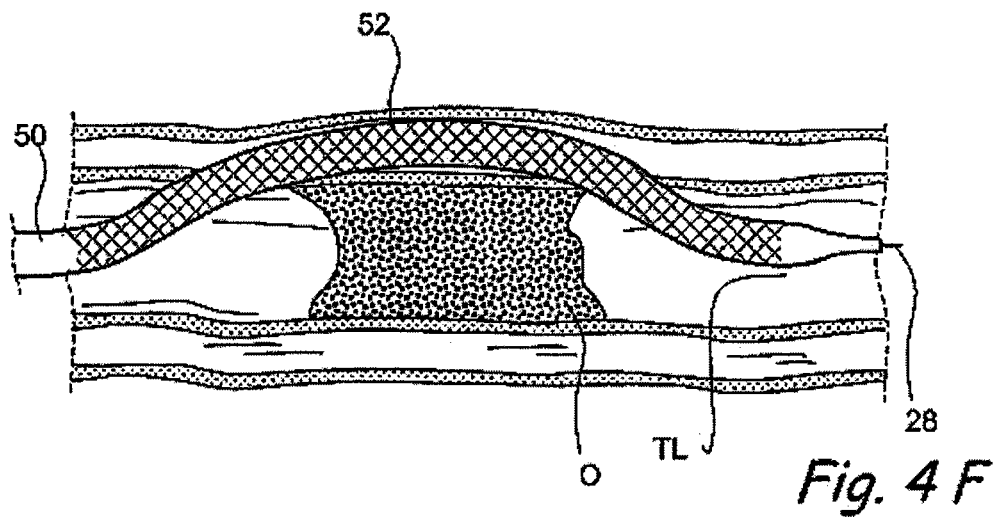
Figure 4:
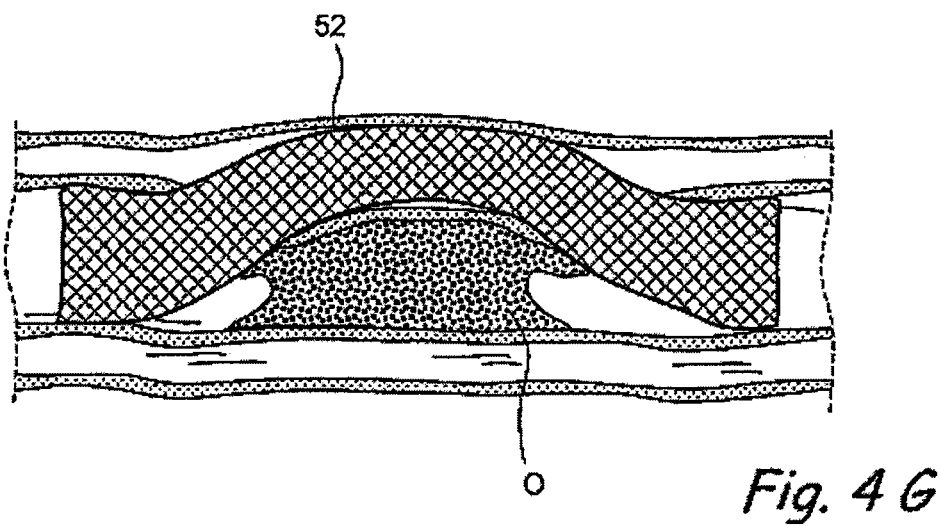

Then, as seen in FIG. 4C, the needle 24 is advanced through adjacent tissue and into the true lumen TL of the artery, distal to the obstruction O.

Thereafter, as shown in FIG. 4D, a, 014 inch guidewire 28 is advanced through the lumen of needle 24 and into the true lumen TL of the artery.

Subsequently, as seen in FIG. 4E, the needle 24 is withdrawn to its retracted position and the catheter 10 as well as the first guidewire 26 are removed, leaving the second guidewire 28 in place such that it extends through the true lumen TL of the artery proximal to (i.e., upstream of) the obstruction O, through the subintimal space, and back into the true lumen TL of the artery distal to (i.e., downstream of) the obstruction O. One or more tract modifying devices (e.g., balloon catheters, atherectomy catheters, etc.) may then be advanced over the guidewire 28 and used to enlarge (e.g., dilate, debulk, bore, etc.) the subintimal space.

Thereafter, as seen in FIG. 4F, after the subintimal space has been enlarged to a desired diameter, a stent delivery catheter 50 may be advanced over the remaining guidewire 28 to position a stent 52 such that it extends from the true lumen TL of the artery proximal to (i.e., upstream of) the obstruction O, through the subintimal space, and back into the true lumen TL of the artery distal to (i.e., downstream of) the obstruction O.

Then, as shown in FIG. 4G, the stent 52 is allowed to self expand, or is plastically deformed to an expanded configuration, and the stent delivery catheter 50 and guidewire 28 are removed, leaving the expanded stent in place. Thus, a stented, subintimal bloodflow channel is formed around the obstruction O.

It is to be further appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. Also, where the steps of a method or process are described, listed or claimed in a particular order, such steps may be performed in any other order unless to do so would render the embodiment or example not novel, obvious to a person of ordinary skill in the relevant art or unsuitable for its intended use. All reasonable additions, deletions, modifications and alterations are to be considered equivalents of the described examples and embodiments and are to be included within the scope of the following claims.

What is claimed is:

1. A method for bypassing an obstruction in a blood vessel that has a true lumen and a vessel wall, and wherein the vessel wall has an intima, said method comprising the steps of:
 (A) advancing a first guidewire through into the blood vessel such that a distal portion of the first guidewire becomes positioned within a subintimal space adjacent to the obstruction;
 (B) providing or obtaining a catheter device that comprises;
 i) an elongate catheter body having a distal end and an outer diameter of no more than 0.080 inch, at least a portion of said catheter body comprising a) a solid core member having at least first and second lumens extending therethrough formed substantially of a material selected form the group consisting of: polyethylene, high density polyethylene, ultra-high molecular weight polyethylene or polypropylene and having at least one lumen extending therethrough, b) a substantially cylindrical braided layer disposed about the core member, said braided layer comprising a material selected from steel and armid fiber c) an outer layer disposed about said braided layer and (d) a distal tip member comprising a composite structure formed on flexible plastic disposed on a rigid housing; and ii) a laterally deployable member having a lumen and a distal end, said laterally deployable member being moveable between a retracted position wherein its distal end resides within a lumen of the core member and an extended position wherein its distal end extends laterally from the catheter body;

(C) advancing the catheter body over the first guidewire and through a sheath of size 6 French or smaller, such that the distal end of the catheter body becomes positioned within the subintimal space;

(D) advancing or extending the laterally deployable member from the catheter body into the true lumen of the blood vessel, distal to the obstruction;

(E) advancing a second guidewire through the lumen of the laterally deployable member and into the true lumen of the blood vessel, distal to the obstruction;

(F) retracting the laterally deployable member;

(G) removing the catheter device and the first guidewire, leaving the second guidewire in place such that it extends through the true lumen of the blood vessel proximal to the obstruction, through the subintimal space and back into the true lumen of the blood vessel distal to the obstruction; and (H) advancing at least one working device over the second guidewire and using said at least one working device to modify the subintimal space to create a patent bypass channel through which blood may flow around the obstruction.

2. A method according to claim 1 wherein the obstruction is a chronic total occlusion of at least one artery.

3. A method according to claim 2 wherein the at least one artery is at least one peripheral artery.

4. A method according to claim 3 wherein the at least one peripheral artery is the iliac artery, the femoral artery, the popliteal artery or a segment of vasculature that includes portion of the femoral and popliteal arteries.

5. A method according to claim 2 wherein the artery is a coronary artery.

6. A method according to claim 1 wherein the catheter device further comprises at least one imageable marker that indicates the direction or trajectory on which the laterally deployable member will advance or extend from the catheter body and wherein Step D further comprises:

imaging the imageable marker and using the resultant image of said marker to make any necessary adjustment of the rotational orientation of the catheter body to thereby increase the likelihood that the laterally deployable member will subsequently advance or extend into the true lumen of the blood vessel rather than to some other location.

7. A method according to claim 1 wherein the catheter device provided in Step D further comprises a housing within which at least a distal portion of the laterally deployable member resides while in its retracted position, said housing being imageable and shaped in a manner that indicates the direction in which the laterally deployable member will extend or advance from the catheter body, and wherein Step D further comprises:

imaging the housing and using the resultant image of said housing to make any necessary adjustment of the rotational orientation of the catheter body to increase the likelihood that the laterally deployable member will subsequently advance or extend into the true lumen of the blood vessel rather than to some other location.

8. A method according to claim 1 wherein Step H comprises advancing a balloon catheter over the second guidewire and using the balloon catheter to dilate the subintimal space.

9. A method according to claim 1 wherein Step H comprises advancing an atherectomy device over the second guidewire and using the atherectomy device to enlarge the subintimal space.

10. A method according to claim 1 wherein Step H comprises advancing a stent over the second guidewire and causing the stent to expand within the subintimal space.

* * * * *